(12) United States Patent
Kuehn

(10) Patent No.: US 6,837,260 B1
(45) Date of Patent: Jan. 4, 2005

(54) PRESSURE SUPPORT SYSTEM HAVING A TWO-PIECE ASSEMBLY

(75) Inventor: Daniel Kuehn, Export, PA (US)

(73) Assignee: Respironics, Inc., Murrysville, PA (US)

( * ) Notice: Subject to any disclaimer, the term of this patent is extended or adjusted under 35 U.S.C. 154(b) by 0 days.

(21) Appl. No.: 09/432,192

(22) Filed: Nov. 2, 1999

(51) Int. Cl.[7] .................. A61M 16/00; A61M 16/20; F16K 27/00; F16K 51/00
(52) U.S. Cl. ............... 137/315.01; 128/204.18; 128/204.21; 128/204.23; 128/205.24; 137/315.04; 137/487; 137/487.5
(58) Field of Search .................. 137/315.04, 486, 137/487, 487.5, 15.17, 15.18, 315.01, 884; 128/204.18, 204.21, 204.23, 205.24

(56) References Cited

U.S. PATENT DOCUMENTS

| | | | | | |
|---|---|---|---|---|---|
| 3,213,883 | A | * | 10/1965 | Carls ........................ | 137/884 |
| 4,080,103 | A | * | 3/1978 | Bird ........................ | 128/204.18 |
| 4,794,922 | A | * | 1/1989 | DeVries ................ | 128/204.18 |
| 4,826,510 | A | * | 5/1989 | McCombs ............ | 128/204.18 |
| 4,840,171 | A | * | 6/1989 | Rohling et al. ........ | 128/204.18 |
| 4,898,174 | A | * | 2/1990 | Fangrow, Jr. .......... | 128/205.24 |
| 4,909,247 | A | * | 3/1990 | Terrisse et al. ........ | 128/206.27 |
| 4,921,072 | A | * | 5/1990 | Divisi ...................... | 137/884 |
| 4,949,715 | A | * | 8/1990 | Brugger ................ | 128/204.21 |
| 5,181,692 | A | * | 1/1993 | Brausfeld .............. | 137/315.01 |
| 5,299,565 | A | * | 4/1994 | Brown .................... | 128/204.18 |
| 5,611,372 | A | * | 3/1997 | Bauer et al. ................ | 137/884 |
| 5,645,054 | A | * | 7/1997 | Cotner et al. .......... | 128/204.23 |
| 5,655,522 | A | * | 8/1997 | Mechlenburg et al. . | 128/204.23 |
| 5,673,687 | A | * | 10/1997 | Dobson et al. ........ | 128/204.14 |
| 5,694,923 | A | * | 12/1997 | Hete et al. ............. | 128/204.18 |
| 6,016,838 | A | * | 1/2000 | Wigmore .................... | 137/884 |
| 6,152,134 | A | * | 11/2000 | Webber et al. ......... | 128/205.24 |
| 6,216,691 | B1 | * | 4/2001 | Kenyon et al. ........ | 128/204.18 |
| 6,318,360 | B1 | * | 11/2001 | Attolini ................ | 128/204.24 |
| 6,427,690 | B1 | * | 8/2002 | McCombs et al. ..... | 128/205.24 |
| 6,543,449 | B1 | * | 4/2003 | Woodring et al. ..... | 128/204.18 |

* cited by examiner

*Primary Examiner*—George L. Walton
(74) *Attorney, Agent, or Firm*—Michael W. Haas

(57) ABSTRACT

A pressure support system that includes a first housing member and a second housing member. The first housing member has a first plurality of cavities defined therein, and the second housing member has a second plurality of cavities defined therein. The first and second plurality of cavities cooperate to define (a) a first chamber adapted to receive a first component of the pressure support system, (b) a second chamber adapted to receive a second component of the pressure support system, and (c) a first conduit connecting the first component and the second in fluid communication when the first and second housing members are assembled. A fastening system secures the first and second housing members in an assembled relation.

15 Claims, 5 Drawing Sheets

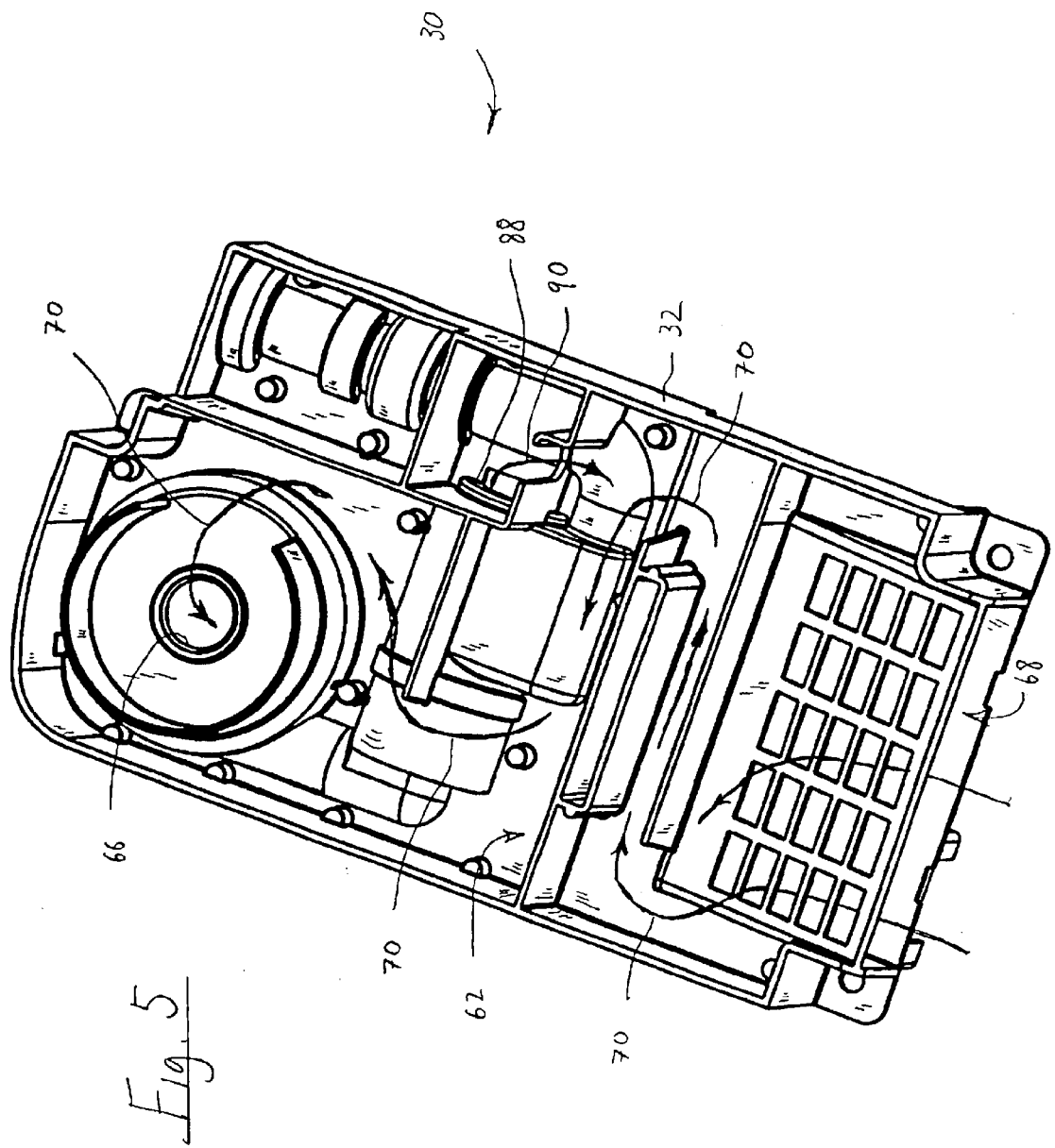

PRESSURE SUPPORT SYSTEM HAVING A TWO-PIECE ASSEMBLY

BACKGROUND OF THE INVENTION

1. Field of the Invention

The present invention pertains to a pressure support system, and, in particular, to a pressure support system having a two-piece assembly that houses at least one component of the pressure support system and that defines at least one fluid connection for carrying gas to or from this component.

2. Description of the Related Art

Pressure support systems that provide a flow of gas to an airway of a patient at an elevated pressure via a patient circuit to treat a medical disorder are well known. For example, it is known to use a continuous positive airway pressure (CPAP) device to supply a constant positive pressure to the airway of a patient to treat obstructive sleep apnea (OSA). It is also known to provide a positive pressure therapy in which the pressure of gas delivered to the patient varies or is synchronized with the patient's breathing cycle or with the patient's respiratory effort to maximize the therapeutic affect and comfort to the patient. It is further known to provide a positive pressure therapy in which the pressure provided to the patient changes based on the detected conditions of the patient, such as whether the patient is snoring or experiencing an apnea, hypopnea or upper airway resistance.

Such conventional pressure support devices typically include a housing containing a pressure generator, for example, a blower, fan, piston, or bellows. The pressure generator creates flow of breathing gas at a pressure greater than ambient atmospheric pressure. Gas from a source of breathing gas, such as air from the ambient atmosphere, is provided to a first external coupling on the housing, such as an inlet vent. A pathway within the housing from the inlet vent to the inlet of the pressure generator delivers the gas from the gas source to the pressure generator, where the elevated pressure gas is created. The outlet of the pressure generator is coupled to a second external coupling on the housing via an exit pathway within the housing that connects the outlet of the pressure generator to the second external coupling. Typically, a flexible tubing from the outlet of the pressure generator to the second external coupling serves as this exit pathway from the outlet of the pressure generator the second external coupling on the housing.

The patient circuit couples to the second external coupling to deliver the elevated pressure breathing gas to the airway of the patient. Typically, the patient circuit includes a flexible conduit having one end coupled to the second external coupling on the pressure support system housing and another end coupled to a patient interface device. The patient interface connects the patient circuit with the airway of the patient to deliver the elevated pressure gas flow to the patient's airway. Examples of patient interface devices include a nasal mask, nasal and oral mask, full face mask, nasal cannula, oral mouthpiece, tracheal tube, endotracheal tube, hood, etc.

More sophisticated pressure support devices include one or more sensors that monitor the pressure or flow of gas to the patient or the conditions of the patient so that the pressure or flow provided to the patient can be controlled based on these detected conditions. In some devices, a flow sensor is also provided downstream of the pressure generator. Typically, such a flow sensor includes a flow element provided in the exit pathway between the outlet of the pressure generator and the external coupling on the housing the pressure support system. The flow elements creates a pressure drop in the exit pathway so that the pressure differential can be measured and used to calculate the rate of flow of gas to or from the patient. In other conventional flow sensors, the flow element causes a portion of the flow of gas in the exit pathway to be diverted through a mass flow sensor to calculate the rate of flow of gas to or from the patient.

There are several techniques for controlling the pressure or flow of breathing gas provided to the patient by the pressure support device. One conventional pressure control method involves providing a pressure control valve assembly in the exit pathway downstream of the pressure generator to exhaust a portion of the breathing gas output by the pressure generator through an exhaust conduit, thereby decreasing the pressure and flow delivered to the patient. Typically, a flexible or rigid fluid delivery conduit couples the output of the pressure generator to the pressure control valve within the housing of the pressure support system. A similar conduit connects the output of the pressure control valve to the external output coupling on the housing of the pressure support device.

Another conventional pressure control method involves controlling the motor speed of the pressure generator, such as the motor speed of a blower that is used to create a flow of gas, so that the pressure generator outputs the gas at the desired rate or pressure without an additional pressure control valve. It is also known to use a combination of the pressure control valve and motor speed control to control the pressure or flow of breathing gas output to the patient.

It can be appreciated that a conventional pressure support device includes many separate, individual components, such as the pressure generator, pressure control assembly, and flow element. These individual components are assembled in series in fluid communication with one another via flexible or rigid conduits. This requires clamps, glues or other such attachment devices for securing the conduits to the inlet or outlet of the respective component. In addition, the housing for the pressure support system must providing mounting surfaces on which each device is mounted. Assembling the pressure support device thus involves (1) attaching the pressure generator to the housing, (2) attaching the pressure controller to the pressure via a flexible tube, (3) attaching the pressure control to the housing, (4) attaching the flow element to the pressure controller via another flexible tube, (5) attaching the flow element to the housing, and (6) attaching the output of the flow element to the external coupling of the housing.

It can be appreciated that manufacturing a conventional pressure support device is relatively complicated and time consuming. In addition, there is always a chance for leaks where the flexible tube attaches to the pressure generator, pressure control assembly, flow element, or the second external coupling on the pressure support system housing.

SUMMARY OF THE INVENTION

Accordingly, it is an object of the present invention to provide a pressure support system that overcomes the shortcomings of conventional pressure support systems. This object is achieved according to one embodiment of the present invention by providing a pressure support system that includes a first housing member having a first plurality of cavities defined therein and a second housing member having a second plurality of cavities defined therein. When assembled, the first and second plurality of cavities cooperate with one another to define at least one chamber that receives a component of the pressure support system, such as the pressure generator, pressure control assembly, or flow element. When assembled, the first and second plurality of cavities also cooperate with one another to define at least one conduit connected to such a component to communicate gas therewith. A fastening system secures the first and second housing members in the assembled relation. Thus, the present invention avoids the need for assembling the various components of the pressure support system to one another using conduits and conduit attaching elements.

This and other objects, features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

BRIEF DESCRIPTION OF THE DRAWINGS

FIG. 5 is a perspective view of the bottom of the first housing member in the two-piece housing.

DETAILED DESCRIPTION OF THE PRESENTLY

PREFERRED EMBODIMENTS OF THE INVENTION

Figure 1:
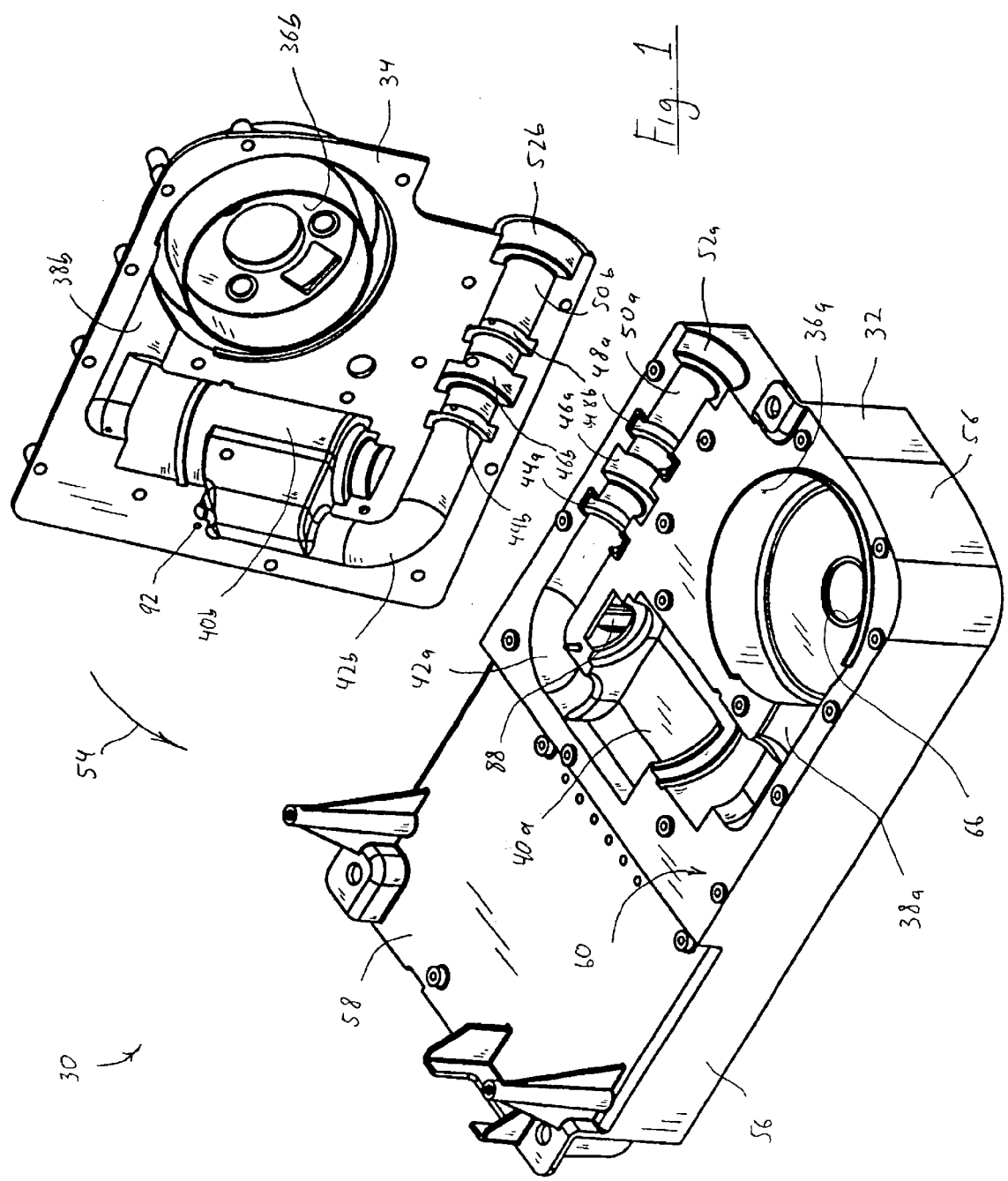
FIG. 1 is a perspective view of a pressure support system according to the principles of the present invention illustrating the two-piece housing in an unassembled configuration.
Figure 2:
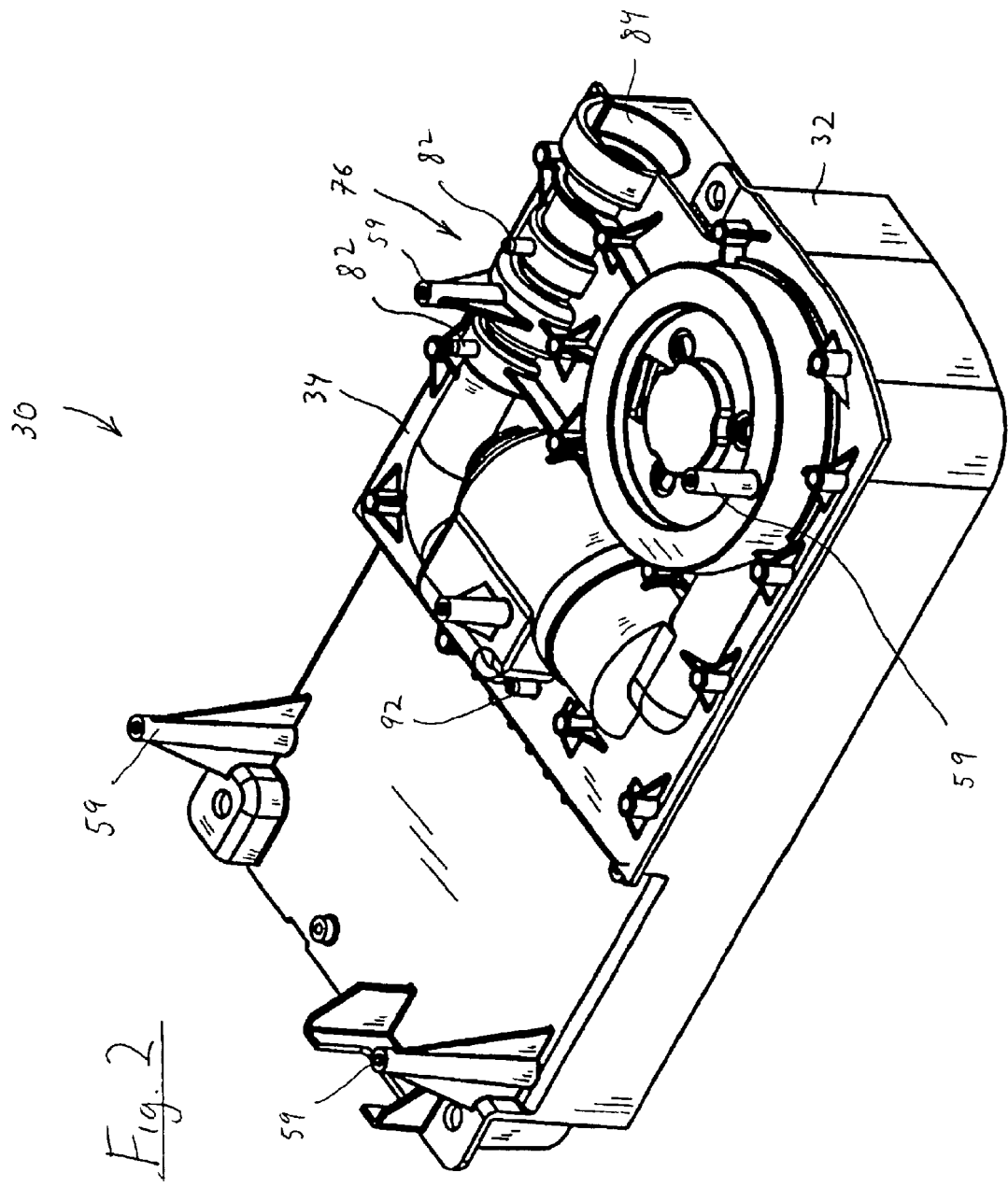
FIG. 2 is a perspective view of the pressure support system of FIG. 1 illustrating the two-piece housing in an assembled configuration.

FIGS. 1 and 2 are perspective views of a pressure support system 30 according to the principles of the present invention. Pressure support system 30 includes a first housing member 32 and a second housing member 34, which are shown in an unassembled configuration in FIG. 1 and in an assembled configuration in FIG. 2. In an exemplary embodiment of the present invention, first and second housing members 32 and 34 are each defined by a unitary piece of material, such as an injection molded plastic. It is to be understood, that the present invention contemplates other techniques for forming the first and second housing members, such as thermoforming, casting, machining or any other conventional fabrication techniques. It is to be further understood, that the first and second housing member can each be formed from separate pieces of material that are bonded together. In addition, the first and second housing members can be formed from any material suitable for use in pressure support system.

First housing member 32 has a first plurality of cavities 36a, 38a, 40a, 42a, 44a, 46a, 48a, 50a, and 52a defined therein. Similarly, second housing member 34 has a second plurality of cavities 36b, 38b, 40b, 42b, 44b, 46b, 48b, 50b, and 52b defined therein. The first and second plurality of cavities are defined in the respective first and second housing members such that when the first and second housing members are assembled, as indicated by arrow 54, the cavities cooperate to define separate chambers for housing a component of the pressure support system. In addition, when the first and second housing members are assembled, the first and second plurality of cavities define the fluid carrying conduits that deliver gas from one component of the pressure support system to another. In this manner, the pressure support system of the present invention realizes a significant simplification in the manufacturing process in that all of the components of the pressure support system and their interconnections are provided in an easily assembled two-piece housing. This eliminates the need to separately connect each component of the pressure support system with a flexible or rigid conduit, as is typically the case with conventional pressure support devices.

In the illustrated exemplary embodiment, first housing member 32 also defines the base for the pressure support system housing. For example, walls 56 at the peripheral edges of first housing member 32 define the exposed sides of the housing for the pressure support system. In addition, first housing member 32 includes a first area 58 on a first side (top) 60 of the first housing member at which a control circuit or other circuit board can be mounted for securing the circuit to the first housing member. It is to be understood, that other circuit board mounting structures can be provided by the first housing member, the second housing member, or a combination thereof. For example, posts 59 can be used to support a circuit board. A second side 62 (bottom) of first housing member is shown in FIG. 5 and is discussed in greater detail below.

Referring now to the figures, the cooperation of the first and second plurality of cavities and elements defined by this interaction will now be described. When first and second housing members 32 and 34 are assembled, cavities 36a and 36b cooperate to define a pressure generator housing chamber adapted to receive a pressure generating element 64, which in the illustrated embodiment is a centrifugal blower. That is, cavities 36a and 36b each define a half of the pressure generator housing chamber. A blower inlet port 66 is provided in first housing member 32 to communicate a flow of gas from second side 62 to first side 60 of the first housing member.

As shown in FIG. 5, gas from a gas source, such as ambient atmosphere, enters an inlet vent 68 on the second side of the first housing member. A plurality of walls are provided on the second side of the first housing member to define a tortuous path, as indicated by arrows 70, from inlet vent 68 to blower inlet port 66. In a preferred embodiment of the present invention, padding, cushion, foam or other sound insulating materials is provided along the walls of path 70 to dampen noise generated by pressure generator 64.

An outlet of the pressure generator is coupled in fluid communication with a pressure control valve 72 provided in a valve chamber 74. Cavities 38a and 38b in first and second housing members cooperate to define the conduit that connects the outlet of the pressure generator with the inlet of the pressure control valve. Cavities 40a and 40b cooperate to define valve chamber 74. Pressure control valve 72 is any valve that restricts the flow of gas from the pressure generator, exhausts a portion of the flow generated by the pressure generator from the patient circuit, or a combination thereof, to control the pressure or flow of gas delivered to the patient. An example of a suitable pressure control valve is the sleeve valve described in copending U.S. patent application Ser. No. 09/347,071, to Truitt et al., the contents of which are incorporated herein by reference.

In an exemplary embodiment, pressure control valve 72 controls the pressure of gas delivered to the patient by venting or exhausting a portion of the gas received from the pressure generator from the conduit coupling the pressure generator to the patient circuit, by restricting the flow of gas to the patient circuit, or by means of a combination of exhausting and restricting gas. In the illustrated embodiment, a port 88 is provided in the first housing member so that gas can pass from the first side to the second side of the first housing member at valve chamber 74. More specifically, first housing member 32 and port 88 defined therein are configured such that gas passes from valve chamber 74 under the control of the pressure control valve into tortuous path 70 as indicated by arrow 90. This configuration maximizes the noise suppression of the pressure support system.

The illustrated embodiment of the present invention also includes a pressure pick-off port 92 that provides a fluid connection between valve chamber 74 and a pressure sensor. Although pressure pick-off port 92 is illustrated as being in second housing member 34, it is to be understood the pressure pick-off port can be provided in the first housing member. Of course other pressure sensing ports can be provided in the first or second housing.

Figure 3:
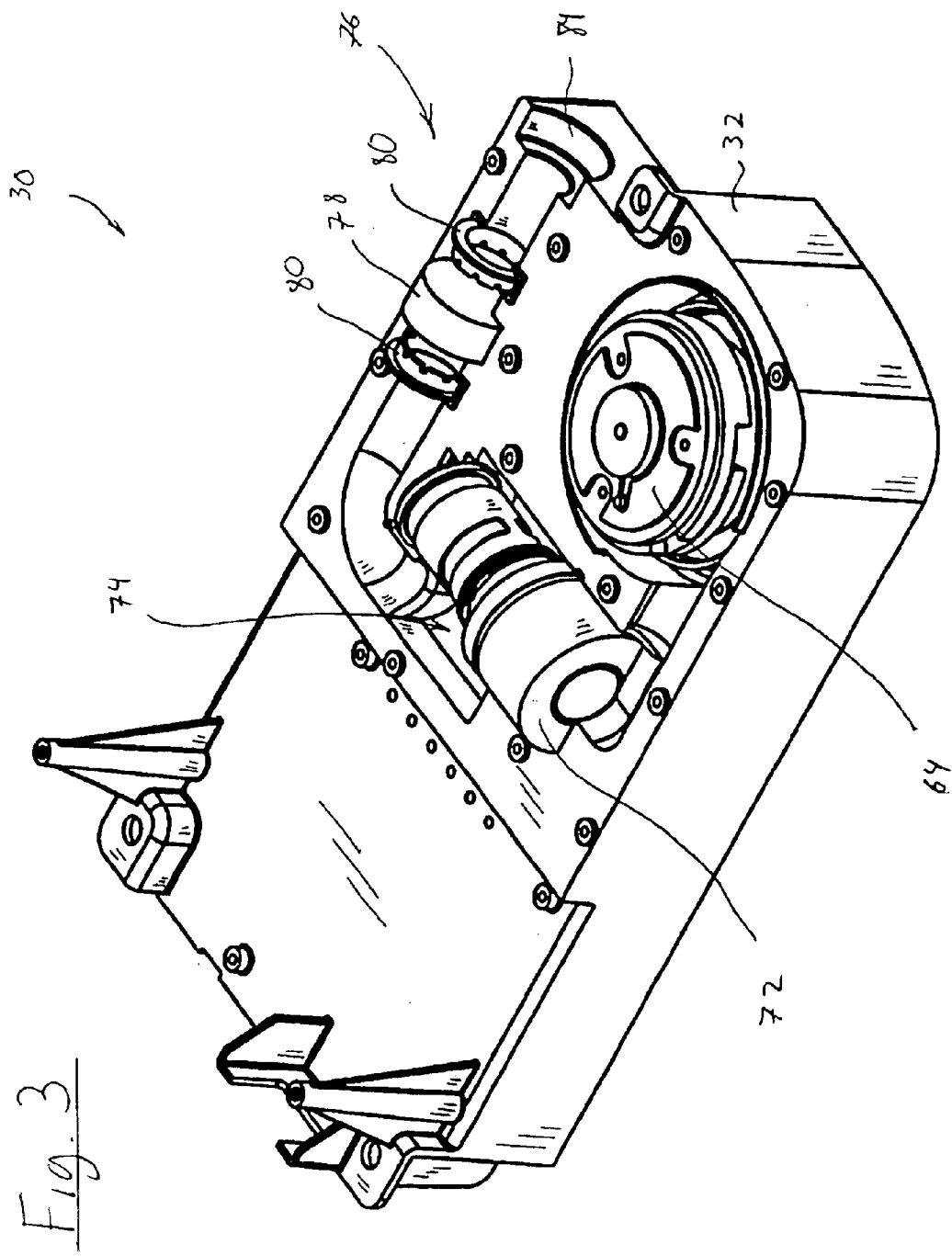
FIG. 3 is a perspective view of a first housing member in the two-piece housing illustrating the placement of various components of the pressure support system in the first housing member.

The outlet of the valve chamber is coupled in fluid communication with a flow sensing assembly, generally indicated at 76. More specifically, cavities 42a and 42b cooperate to define a conduit that communicates the outlet of the valve chamber with the flow sensing assembly. Flow sensing assembly 76 is used to detect the rate of flow of gas in the patient circuit, and includes a flow element 78 and a pair of pressure measurement elements 80. Flow element 78 is a device that creates a flow restriction in the patient circuit so that the pressure differential across the flow element can be measured or so that a secondary stream of gas is diverted through a mass flow sensor in order to determine the flow in the conduit. Pressure measurement elements 80 are rings that encompass the patient circuit and a plurality of orifices defined therein so that gas can pass from the exit pathway to a pressure sensor (not shown) from a plurality of circumferential locations on the patient circuit, as a opposed to a single port from the pressure sensor to one location one the circumference of the patient circuit. Pressure ports 82 on the exposed surface of second housing member 34 provide a coupling to one or more pressure sensors. It is to be understood that one of both the pressure supports can be provided on the first housing member instead of on the second housing member as shown in FIG. 3.

Cavities 44a, 44b and 48a, 48b in first and second housing members cooperate to define the chambers for receiving pressure measurement elements 80. Cavities 46a and 46b cooperate to define a flow element chamber for receiving flow element 78 therein. In addition, cavities 50a and 50b cooperate to define a conduit that couples the output of flow assembly 76 to an external coupling 84 on the housing of the pressure support device. A flexible conduit (not shown) attaches to the external coupling to communicate a flow of gas to the airway of the patient. In the illustrated embodiment, a gasket (not shown) is provided in the circular opening of external coupling 84 and a patient circuit connection piece (not shown) inserts into the gasket for attaching the patient circuit to the external coupling.

Figure 4:
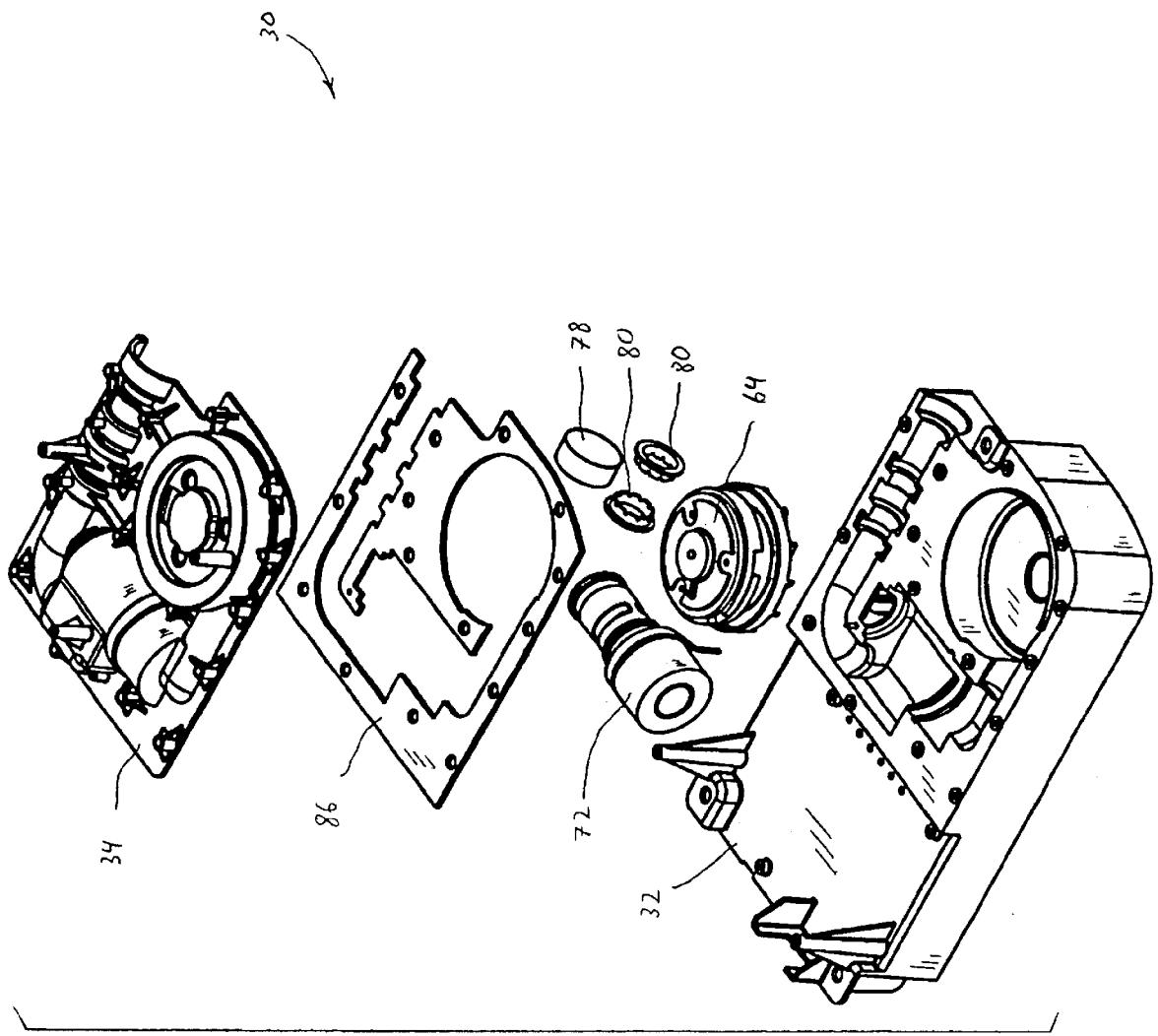
FIG. 4 is an exploded view of a pressure support system according to the principles of the present invention.

FIG. 4 illustrates, in exploded fashion, the components of the pressure support system of the present invention. As shown therein, a presently preferred embodiment of the invention contemplates providing a gasket disposed between the first and second housing members. Gasket 86 is made from a material, such as rubber or foam, that provided a sealed engagement between first and second housing members 32 and 34 so that gas does not leak from the interface between these housing members. In a preferred embodiment, the first and second housing members are maintained in the assembled relation by screws. It is to be understood, however, that the present invention contemplates securing the first and second housing members in the assembled relation using any suitable fastening system, such as nuts/bolts, clamps, snap-fit members, adhesives, and ultrasonic welding.

The present invention contemplates that first and second housing members 32 and 34 can be separate from one another as shown in FIG. 1, for example. However, the present invention also contemplates that the first and second housing members can be initially coupled to one another, for example, in a clam shell configuration, and then closed during the assembly process to house one or more of the various components of the pressure support system discussed above.

Although the pressure support system of the present invention has been described above and is shown in the figures with the valve chamber being downstream of the pressure generator housing chamber and the flow element chamber downstream of the valve chamber, it is to be understood that other arrangements for the chambers in the pressure support system are contemplated by the present invention. For example, the valve chamber can be upstream of the pressure generator housing chamber. In addition, chambers other than those shown in the figures and described above can be provided. For example, a muffler chamber for housing a muffler that receives the exhaust from the pressure control valve can be provided by the cavities defined in the first and second housing members.

It can be appreciated that the above-described two-piece system for forming the pressure support system provides a very efficient method for forming chambers and interconnections for the components of the pressure support system. It also provides a relatively closed system in that the it minimizes the changes that leaks will occur at the interconnections of the components of the pressure support system. However, it also provides access to the gas stream merely by tapping into the first or second housing member. However, the present invention also contemplates accessing the gas stream without making additional holes in either the first or second housing member. For example, a sensor, such as a temperature sensor, can provided between the first and second housing members to measure a characteristic of the gas flow, such as its temperature. This technique is especially suited for relatively flat sensors.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

What is claimed is:

1. A pressure support system comprising:
a first housing member having a first plurality of cavities defined therein;
a second housing member having a second plurality of cavities defined therein, wherein the first and the second plurality of cavities have complimentary configurations such that a cavity from the first plurality of cavities mates with a corresponding cavity from the second plurality of cavities to define a first chamber, a second chamber, and a first conduit responsive to the first and the second housing members being in an assembled relation, and wherein the first conduit operatively connects the first chamber and the second chamber in fluid communication;

a pressure generating element disposed in the first chamber and adapted to generate a flow of breathing gas;

a valve disposed in the second chamber and adapted to control a pressure or a flow of breathing gas output from the pressure generating system, wherein the first conduit connects the pressure generating element and the valve in fluid communication; and a fastening system that secures the first and second housing members in the assembled relation to secure the pressure generating system and the valve within the first and second chambers respectively.

2. A pressure support system according to claim 1, wherein the first housing member and the second housing member are each defined by a single piece of material.

3. A pressure support system according to claim 1, wherein the first and second plurality of cavities cooperate to further define (a) an external coupling and (b) a second conduit operatively connecting the pressure generating element or the valve in fluid communication with the external coupling responsive to the first and the second housing members being in the assembled relation.

4. A pressure support system according to claim 3, further comprising a patient circuit coupled to the external coupling, wherein the patient circuit is adapted to communicate the flow of breathing gas created by the pressure generating element to an airway of a patient.

5. A pressure support apparatus according to claim 1, wherein during normal operation of the pressure support system, the valve is downstream of the pressure generating element.

6. A pressure support system according to claim 1, wherein at least one of the first and the second housing members includes a port defined therein for venting gas discharged by the valve from the valve chamber.

7. A pressure support system according to claim 1, wherein the first and second plurality of cavities further define a third chamber and a second conduit operatively connecting the third chamber to the first chamber or the second chamber, and wherein the pressure support system further comprises:

a flow element disposed in the third chamber, and a pair of flow measurement ports defined through the first housing member or the second housing member on opposite sides of the flow element to enable a pressure differential between the pressure on each side of the flow element to be measured.

8. A pressure support system according to claim 1, further comprising a gasket disposed between the first and second housing members.

9. A pressure support system according to claim 1, wherein the fastening assembly includes a plurality of screws adapted to fix the first and second housing members in the assembled relation.

10. A pressure support system according to claim 1, wherein the first housing member includes a mounting structure adapted to receive a control circuit thereon in a fixed relation.

11. A pressure support system according to claim 1, wherein the first housing member defines a base portion of a housing for the pressure support system.

12. A pressure support system according to claim 11, wherein the first housing member includes:

a first side and a second side, with the first plurality of cavities being defined in the first side of the first housing member;

a blower inlet port adapted to communicate a flow of gas from the second side to the first side of the first housing member;

a plurality of walls extending from the second side of the first housing member, wherein the plurality of walls define:

an inlet vent disposed on the second side adapted to receive gas from ambient atmosphere, and a tortuous path from the inlet vent to the blower inlet port to deliver gas from ambient atmosphere received by the inlet vent to the blower inlet port.

13. A pressure support system according to claim 12, wherein the first housing member includes a port defined therein for venting gas from the conduit to the tortuous path.

14. A pressure support system according to claim 1, further comprising a pressure pick-off port defined in one of the first housing member and the second housing member so as to communicate an interior of the first chamber, the second chamber, or the first conduit with a pressure sensor.

15. A pressure support system comprising:

(a) a first housing member having a first side, a second side, and a first plurality of cavities defined in the first side, the first housing member also having a blower inlet port defined therethrough to communicate a flow of gas from the second side to the first side and a plurality of walls extending from the second side, wherein the plurality of walls define:

(1) an inlet vent disposed on the second side adapted to receive gas from ambient atmosphere, and (2) a tortuous path from the inlet vent to the blower inlet port to deliver gas from ambient atmosphere received by the inlet vent to the blower inlet port;

(b) a second housing member having a second plurality of cavities defined therein, wherein the first and second plurality of cavities have complimentary configurations such that a cavity from the first plurality of cavities mates with a corresponding cavity from the second plurality of cavities to define (a) a first chamber adapted to receive a first component of the pressure support system, (b) a second chamber adapted to receive a second component of the pressure support system, and (c) a first conduit operatively connecting the first component and the second component in fluid communication responsive to the first and the second housing members being in an assembled relation, wherein the first plurality of cavities define a first portion of the first chamber, the second chamber, and the first conduit, and wherein the second plurality of cavities define a remaining portion of the first chamber, the second chamber, and the first conduit responsive to the first and the second housing members being in the assembled relation; and (c) a fastening system that secures the first and second housing members in the assembled relation.

* * * * *